United States Patent
Halac et al.

(10) Patent No.: US 9,681,866 B2
(45) Date of Patent: Jun. 20, 2017

(54) SUTURE LOCKING DEVICE AND METHODS

(75) Inventors: Jason M. Halac, Solara Beach, CA (US); James A. McCrea, Burlingame, CA (US); Troy T. White, Maple Grove, MN (US); Bernhard Kaeferlein, Champlin, MN (US); Ali Hassan, Palo Alto, CA (US); Zihan Lin, Irvine, CA (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 740 days.

(21) Appl. No.: 13/472,799

(22) Filed: May 16, 2012
(Under 37 CFR 1.47)

(65) Prior Publication Data

US 2013/0079802 A1    Mar. 28, 2013

Related U.S. Application Data

(60) Provisional application No. 61/487,633, filed on May 18, 2011.

(51) Int. Cl.
*A61B 17/04* (2006.01)

(52) U.S. Cl.
CPC ...... *A61B 17/0487* (2013.01); *A61B 17/0467* (2013.01); *A61B 17/0485* (2013.01); *A61B 2017/0488* (2013.01)

(58) Field of Classification Search
CPC ........ A61B 17/0467; A61B 2017/0488; A61B 17/0487; A61B 17/0485
USPC ....... 606/232, 139, 144, 148, 167, 170, 103, 606/300
See application file for complete search history.

(56) References Cited

U.S. PATENT DOCUMENTS

| | | | |
|---|---|---|---|
| 5,630,824 A * | 5/1997 | Hart | 606/139 |
| 5,643,292 A | 7/1997 | Hart | |
| 5,902,321 A * | 5/1999 | Caspari et al. | 606/232 |
| 6,059,800 A | 5/2000 | Hart et al. | |
| 6,200,329 B1 | 3/2001 | Fung et al. | |
| 2001/0008971 A1* | 7/2001 | Schwartz et al. | 606/232 |
| 2003/0120287 A1* | 6/2003 | Gross et al. | 606/148 |
| 2003/0144673 A1 | 7/2003 | Onuki et al. | |
| 2003/0167062 A1* | 9/2003 | Gambale et al. | 606/138 |
| 2004/0044366 A1* | 3/2004 | Bonutti | A61B 17/0487 606/232 |
| 2004/0254598 A1* | 12/2004 | Schumacher et al. | 606/170 |
| 2007/0005081 A1 | 1/2007 | Findlay, III et al. | |
| 2007/0093858 A1 | 4/2007 | Gambale et al. | |
| 2007/0270908 A1 | 11/2007 | Stokes et al. | |

(Continued)

FOREIGN PATENT DOCUMENTS

EP    1884207 A1    2/2008

*Primary Examiner* — Jing Ou
(74) *Attorney, Agent, or Firm* — Holland & Hart

(57) ABSTRACT

A suture locking device includes a carrier member, a locking assembly, a suture path, and an actuator assembly. The locking assembly includes a first locking member having an outer surface portion, and a second locking member having an inner surface portion. The suture path is receptive of a suture and defined at least partially through the first locking member, between the outer and inner surface portions, and at least partially through the carrier member. The actuator assembly is operable to move the first and second locking members together to lock the suture relative to the lock assembly.

11 Claims, 16 Drawing Sheets

(56) References Cited

U.S. PATENT DOCUMENTS

2008/0234729 A1\* 9/2008 Page et al. .................... 606/232
2009/0069847 A1 3/2009 Hashiba et al.
2009/0292321 A1\* 11/2009 Collette ................ A61F 2/0811
   606/303
2009/0312795 A1\* 12/2009 Barbieri et al. .............. 606/232

\* cited by examiner

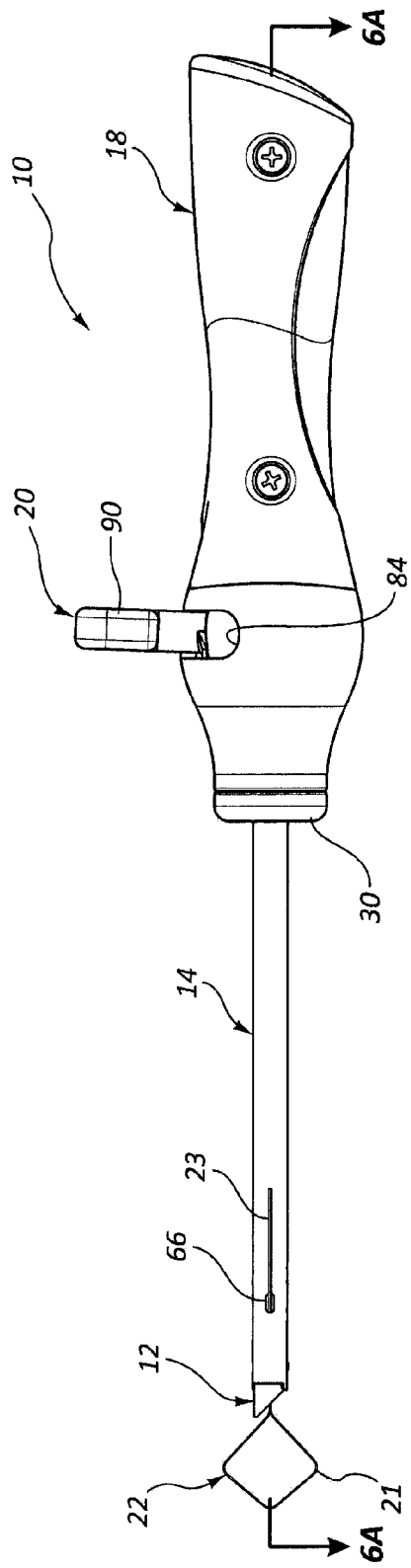
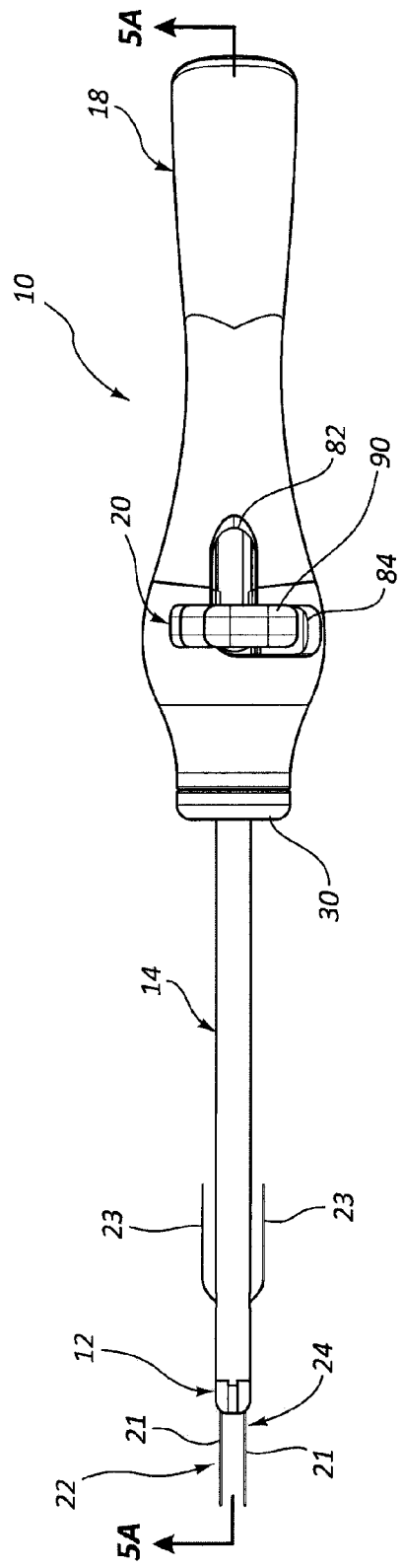
FIG. 3
FIG. 4

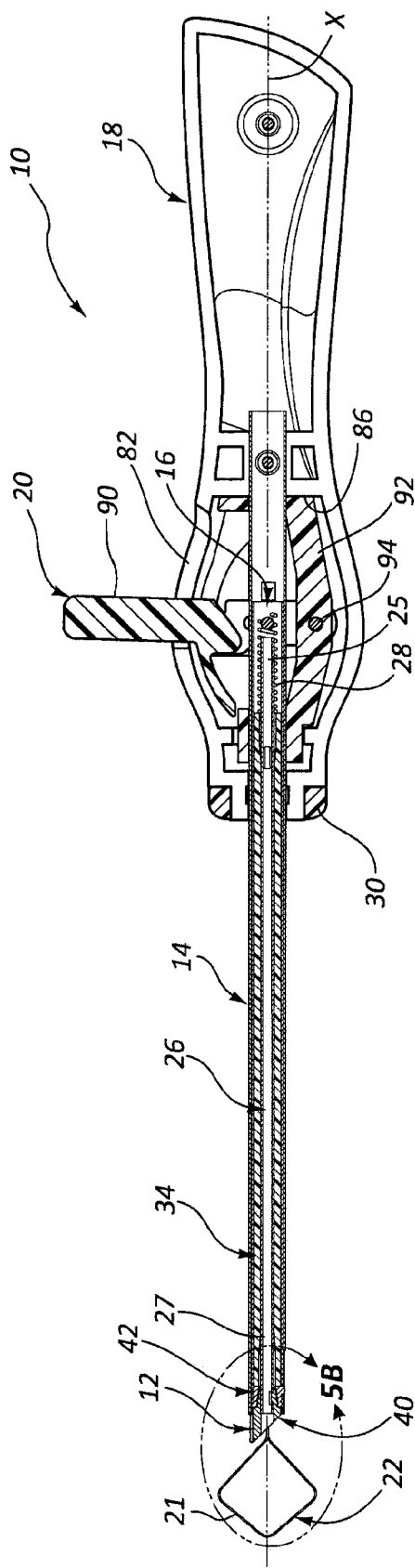
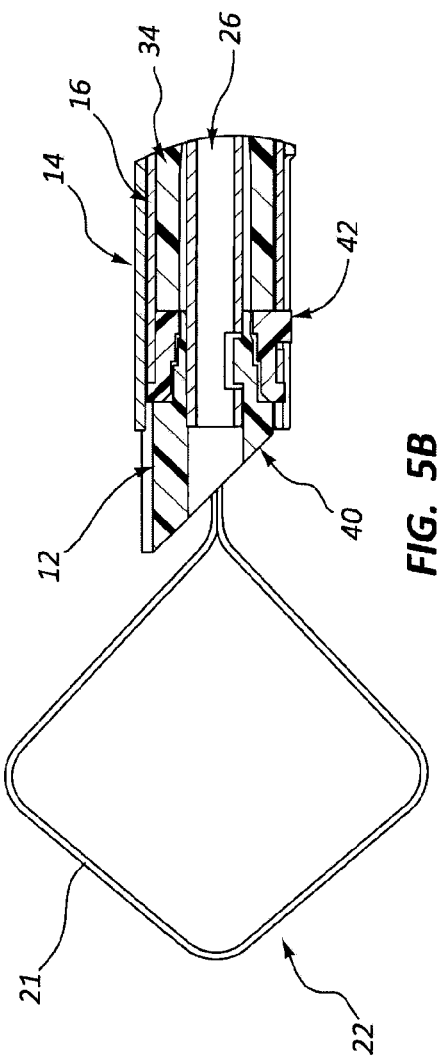
FIG. 5A
FIG. 5B

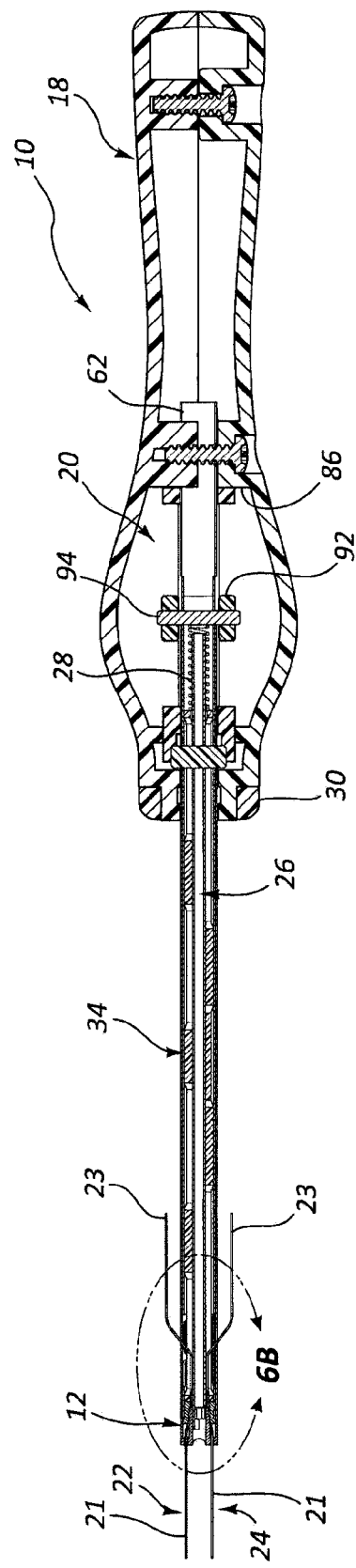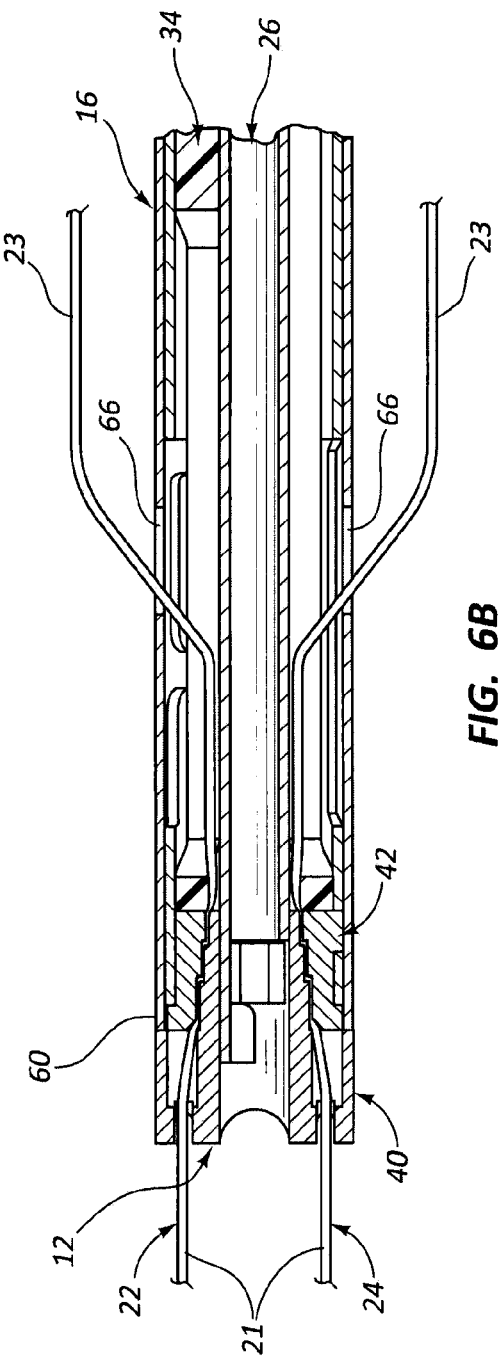
FIG. 6A
FIG. 6B

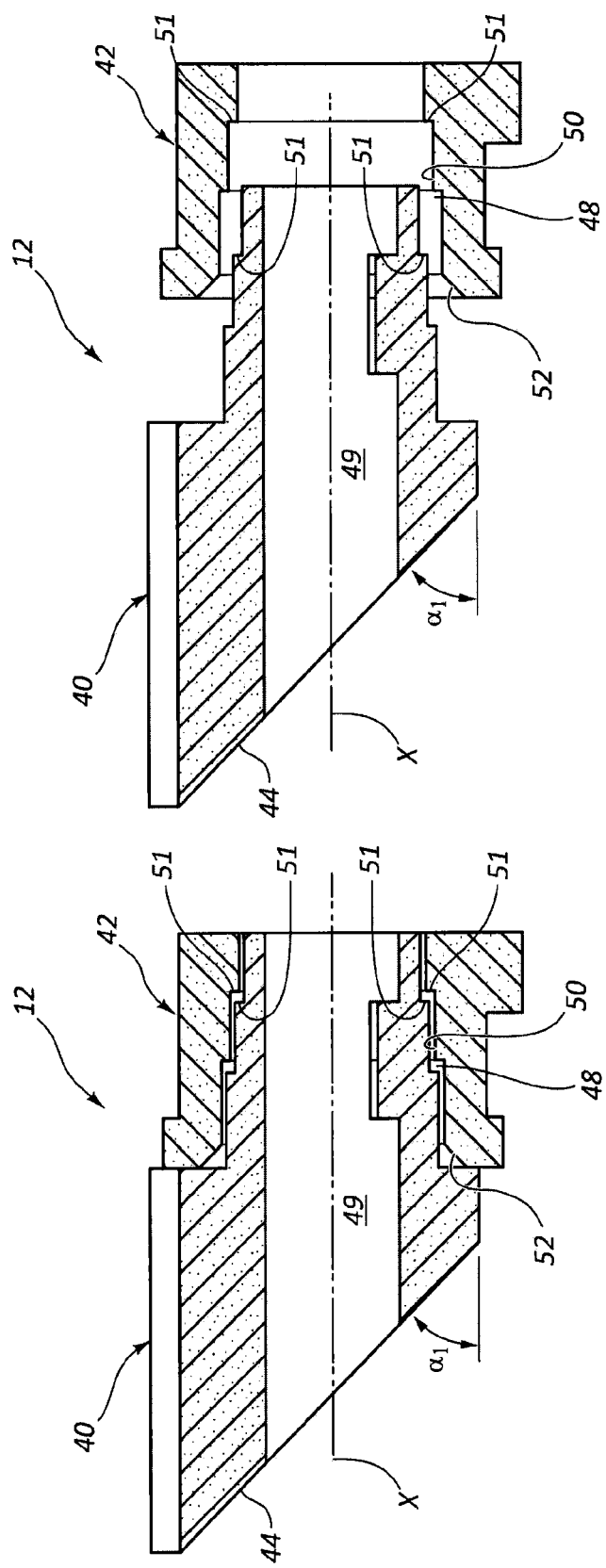

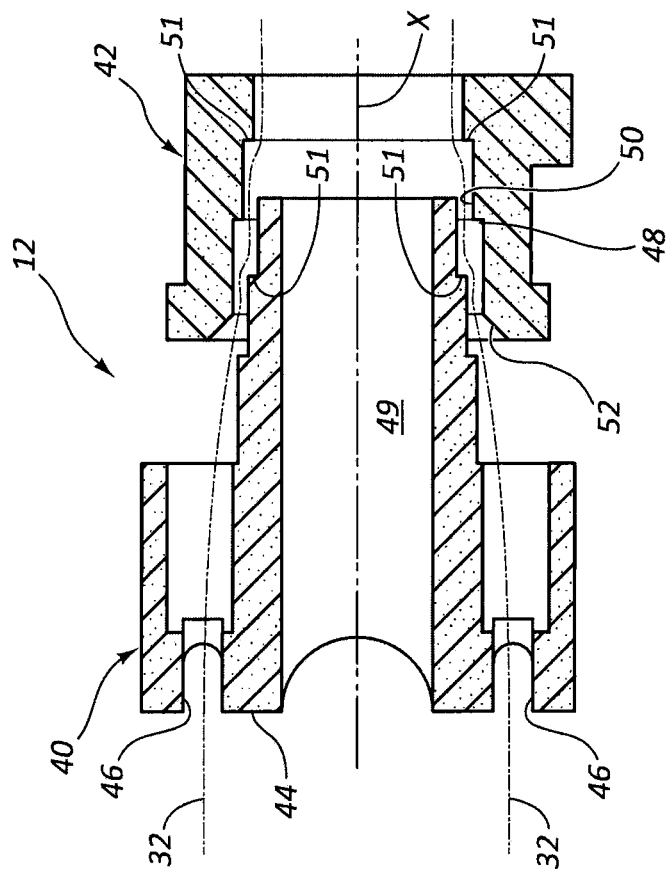
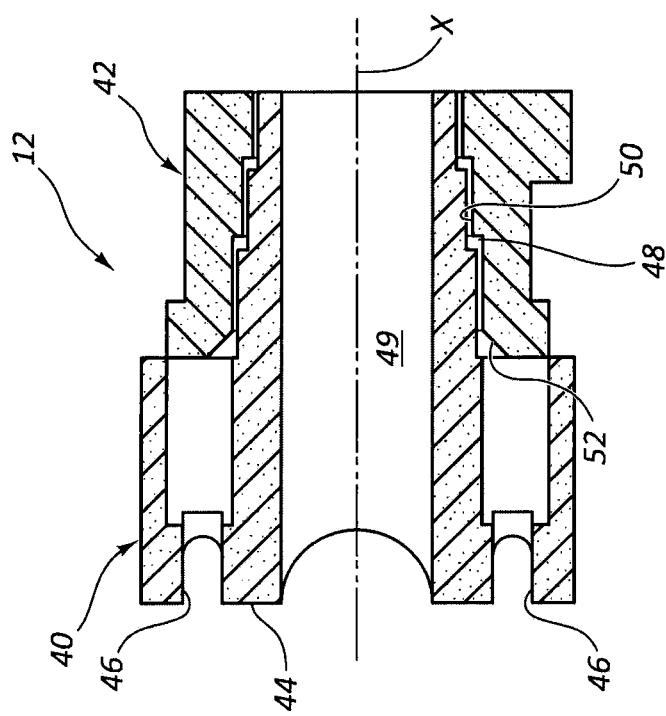

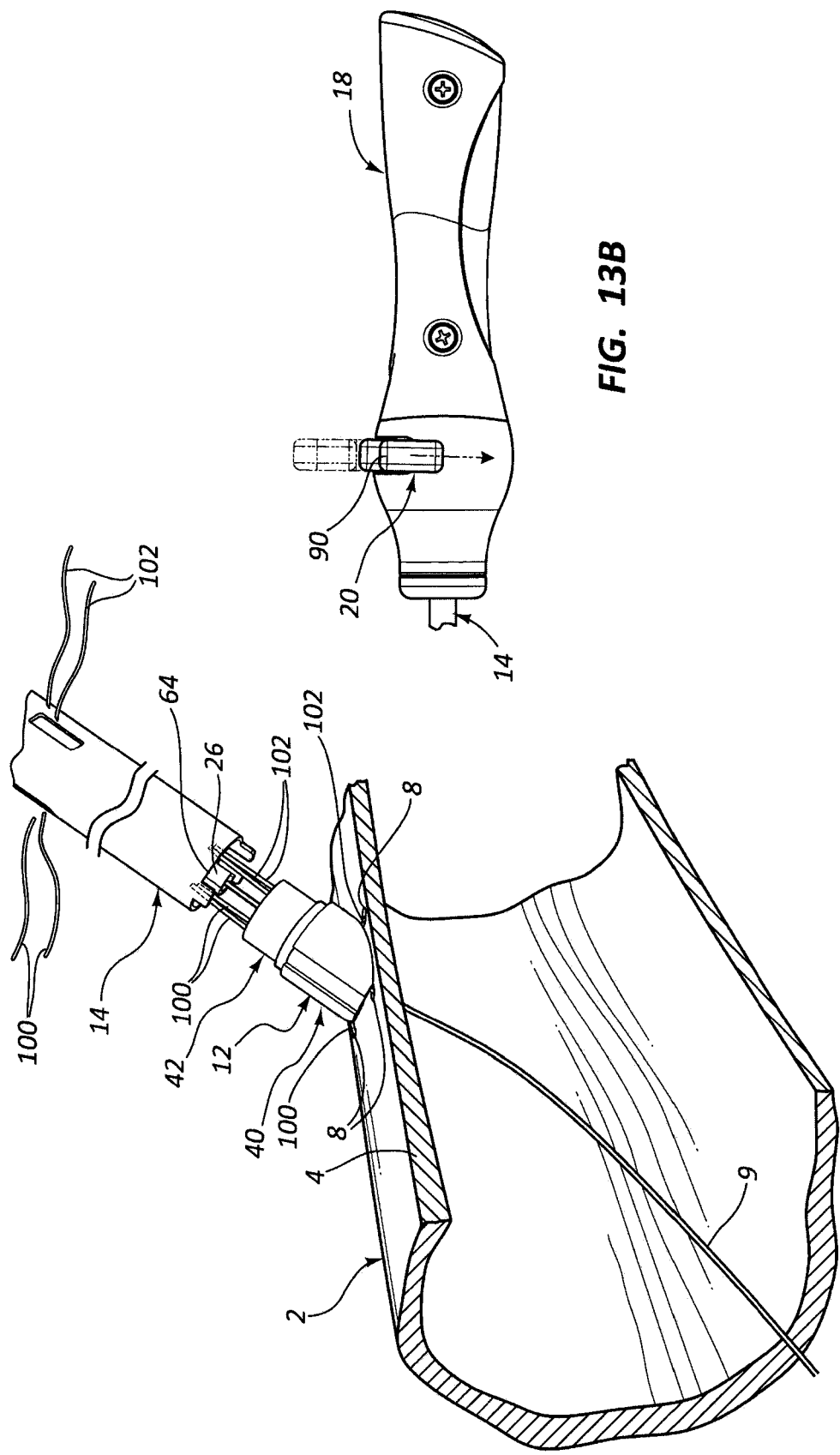

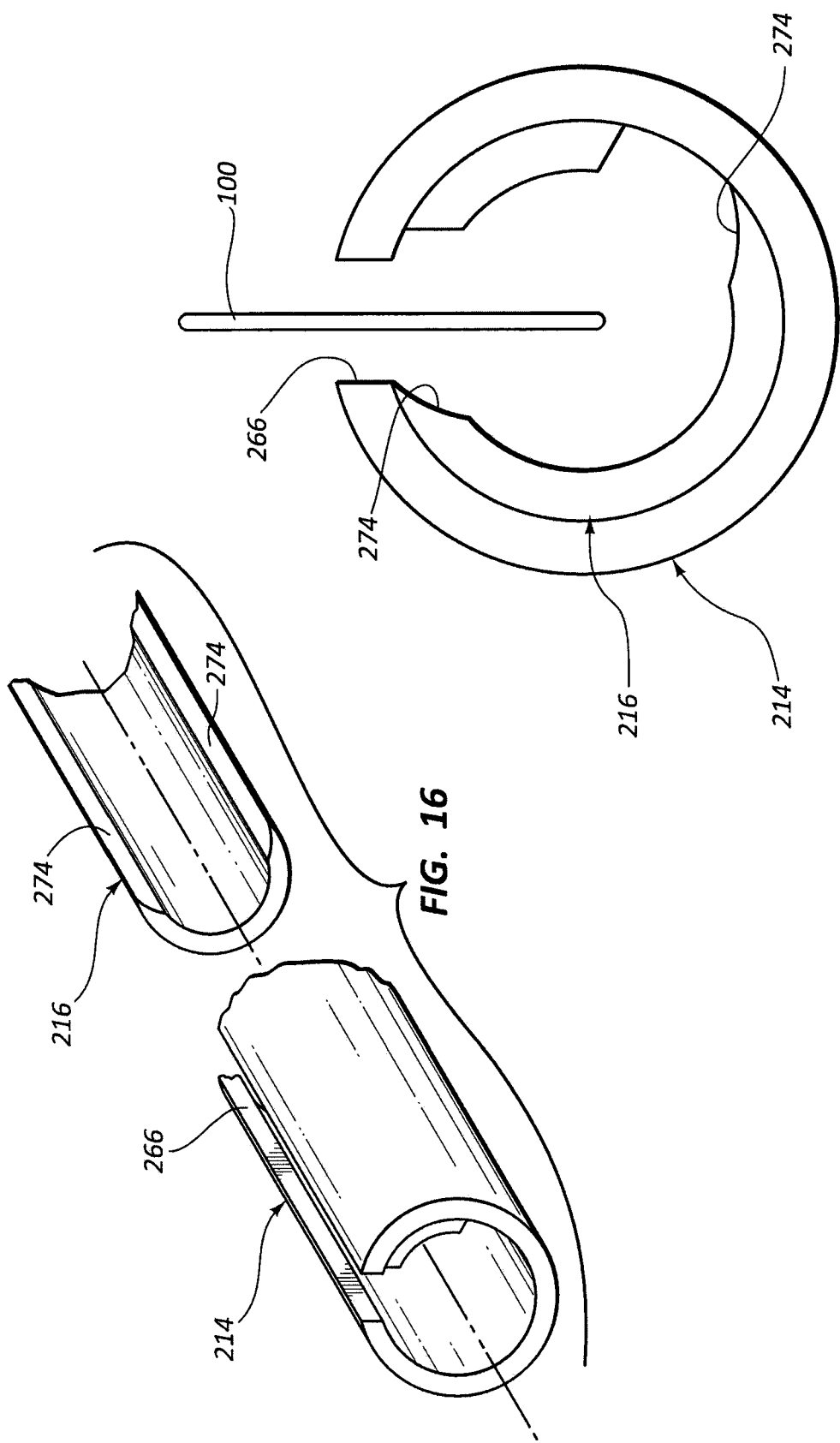

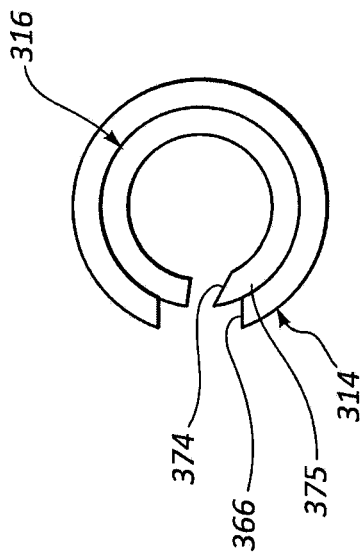
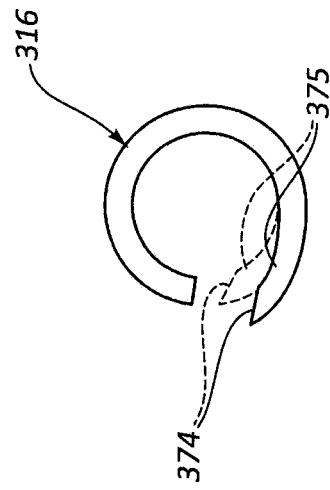
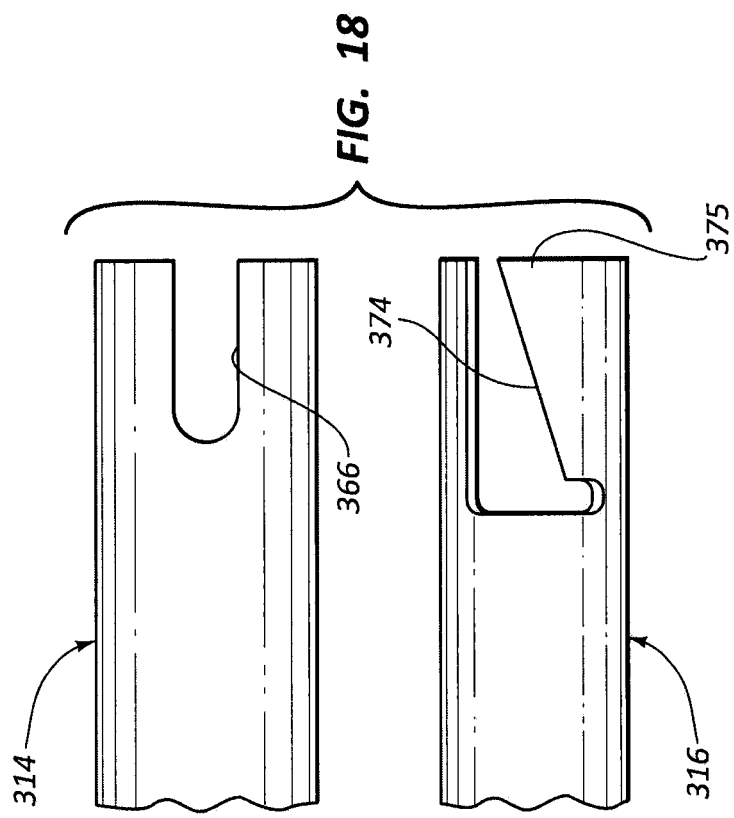

SUTURE LOCKING DEVICE AND METHODS

RELATED APPLICATION

This claims the benefit of U.S. Provisional Application No. 61/487,633, filed on 18 May 2011, which is hereby incorporated by reference herein in its entirety.

TECHNICAL FIELD

The present disclosure relates to closure devices, and more specifically relates to closure devices that hold a vessel opening closed using sutures.

BACKGROUND

Various medical procedures, particularly cardiology procedures, involve accessing a corporeal vessel through a percutaneous sheath. The sheath necessarily requires the formation of a hole or opening in the vessel wall so that a medical procedure may be performed via the sheath. After the particular medical procedure has been performed, the sheath must eventually be removed from the vessel and the access hole in the vessel wall must be closed.

A number of prior vascular closure devices have been developed in attempting to provide a solution for the problem of closing a hole in the vessel wall. Tissue approximation typically involves passing a length of suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

U.S. Pat. Nos. 5,643,292 and 6,059,800 disclose example prior suturing devices used for approximating tissue surrounding the opening in a vessel wall. Most prior closure devices enlarge the vessel opening thereby negating the benefits of using smaller or less invasive percutaneous products. Prior suturing devices are also relatively complicated and difficult to use.

There remains a need, therefore, to provide a suturing apparatus that is relatively simple in construction, is easy to use, and can effectively approximate tissue surrounding an opening in a vessel wall. There is also a need to provide a suturing device that minimizes invasiveness of the suturing procedure.

SUMMARY

One aspect of the present disclosure is directed to a suture locking device that includes a carrier member, a locking assembly, a suture path, and an actuator assembly. The locking assembly includes a first locking member having an outer surface portion, and a second locking member having an inner surface portion. The suture path is receptive of a suture and defined at least partially through the first locking member, between the outer and inner surface portions, and at least partially through the carrier member. The actuator assembly is operable to move the first and second locking members together to lock the suture relative to the lock assembly.

The outer and inner surface portions may define mating stepped features. The suture path may exit through a sidewall of the carrier member proximal of the lock assembly. The suture locking device may include a handle positioned at a proximal end of the carrier member, wherein the actuator assembly includes an actuator lever mounted to the handle. The suture locking device may include a cutting device mounted to the carrier member and operable to cut the suture. The cutting device may be operable by the actuator assembly to cut the suture within the carrier member. The cutting device may be operable to cut the suture only after the suture is locked relative to the locking assembly. The suture locking device may include at least one snare operable to pull the suture into the suture locking device along the suture path.

Another aspect of the present disclosure relates to a suture locking device that includes a locking assembly, a suture cutting member, and an actuator. The actuator is operable to lock a suture with the suture locking assembly when in a first actuated position, and operable to cut the suture with the suture cutting member when in a second actuated position.

The first actuated position may be a longitudinally advanced position, and the second actuated position may be a laterally rotated position. The suture locking assembly may include first and second locking members that define a suture path between an outer surface of the first locking member and an inner surface of the second locking member. The outer surface and inner surface may be configured to provide an interference fit connection between the first and second locking members. The suture locking device may include a carrier member, wherein the suture locking assembly is releasably mounted at a distal end of the carrier member. Operating the actuator to cut the suture may concurrently release the suture locking assembly from the carrier member.

A further aspect of the present disclosure relates to a method of locking a suture across a vessel opening. The method includes providing a suture locking device having a locking assembly, a carrier member, an actuator, and a cutting member. The method includes passing the suture through the locking assembly, operating the actuator to lock the locking assembly to the suture, operating the actuator to cut the suture with the cutting member proximal of the locking assembly, and detaching the locking assembly from the carrier member.

The locking assembly may include first and second locking members, and operating the actuator to lock the locking assembly to the suture includes capturing the suture between the first and second locking members. Operating the actuator to cut the suture with the cutting member may include rotating the cutting member relative to the carrier member. Cutting the suture and detaching the locking assembly may include rotating the actuator about a longitudinal axis of the suture locking device.

The suture locking device may include a handle mounted at a proximal end of the carrier member and the actuator may include a lever mounted to the handle. Operating the actuator to lock the locking assembly may include moving the lever longitudinally relative to the handle, and operating the actuator to cut the suture may include rotating the lever laterally relative to the handle. Passing the suture through the locking assembly may include grasping the suture with a snare and pulling the suture through the locking assembly with the snare.

Another aspect of the present disclosure is directed to a method of operating a suture locking device that includes providing the suture locking device with a locking assembly, a carrier member, an actuator, and a cutting member. The locking assembly includes first and second locking members and is mounted to the carrier member. The method includes operating the actuator to connect the first and second locking members in a locked position, operating the actuator to move the cutting member relative to the carrier member, and disconnecting the locking assembly from the carrier member.

The actuator may include a lever mounted to a handle of the suture locking device, and operating the actuator to move the first and second locking members into a locked position may include advancing the lever distally relative to the handle. Operating the actuator to move the cutting member may include rotating the lever relative to the handle.

The foregoing and other features, utilities, and advantages of the invention will be apparent from the following detailed description of the invention with reference to the accompanying drawings.

BRIEF DESCRIPTION OF THE DRAWINGS

FIG. 3 is a side view of the suture locking device of FIG. 1.

FIG. 4 is a top view of the suture locking device of FIG. 1.

FIG. 5 is a cross-sectional view of the suture locking device of FIG. 4 taken along cross-section indicators 5-5.

FIG. 6A is a cross-sectional view of the suture locking device of FIG. 3 taken along cross-section indicators 6A-6A.

FIG. 6B is a detailed view of a distal end of the suture locking device of FIG. 6A.

FIG. 8A is a cross-sectional view of the locking assembly of FIG. 7 taken along cross-section indicators 8A-8A in an unlocked position.

FIG. 8B is a cross-sectional view of the locking assembly of FIG. 8A in a locked position.

FIG. 9A is a cross-sectional view of the locking assembly of FIG. 7 taken along cross-section indicators 9A-9A in an unlocked position.

FIG. 9B is a cross-sectional view of the locking assembly of FIG. 9A in a locked position.

FIG. 13A shows the suture locking device of FIG. 12A detached from the locking assembly with the pair of sutures cut.

FIG. 13B illustrates an actuator assembly position corresponding to the state of the suture locking device shown in FIG. 13A.

FIG. 16 is an exploded perspective view of another example cutting arrangement according to the present disclosure.

FIG. 17 is an end view of the cutting arrangement of FIG. 16 assembled together.

FIG. 18 is a side view of another example cutting arrangement according to the present disclosure.

FIG. 19 is an end view of the cutting arrangement shown in FIG. 18 assembled together.

FIG. 20 is an end view of the cutting device of FIGS. 18 and 19.

DETAILED DESCRIPTION

Figure 1:
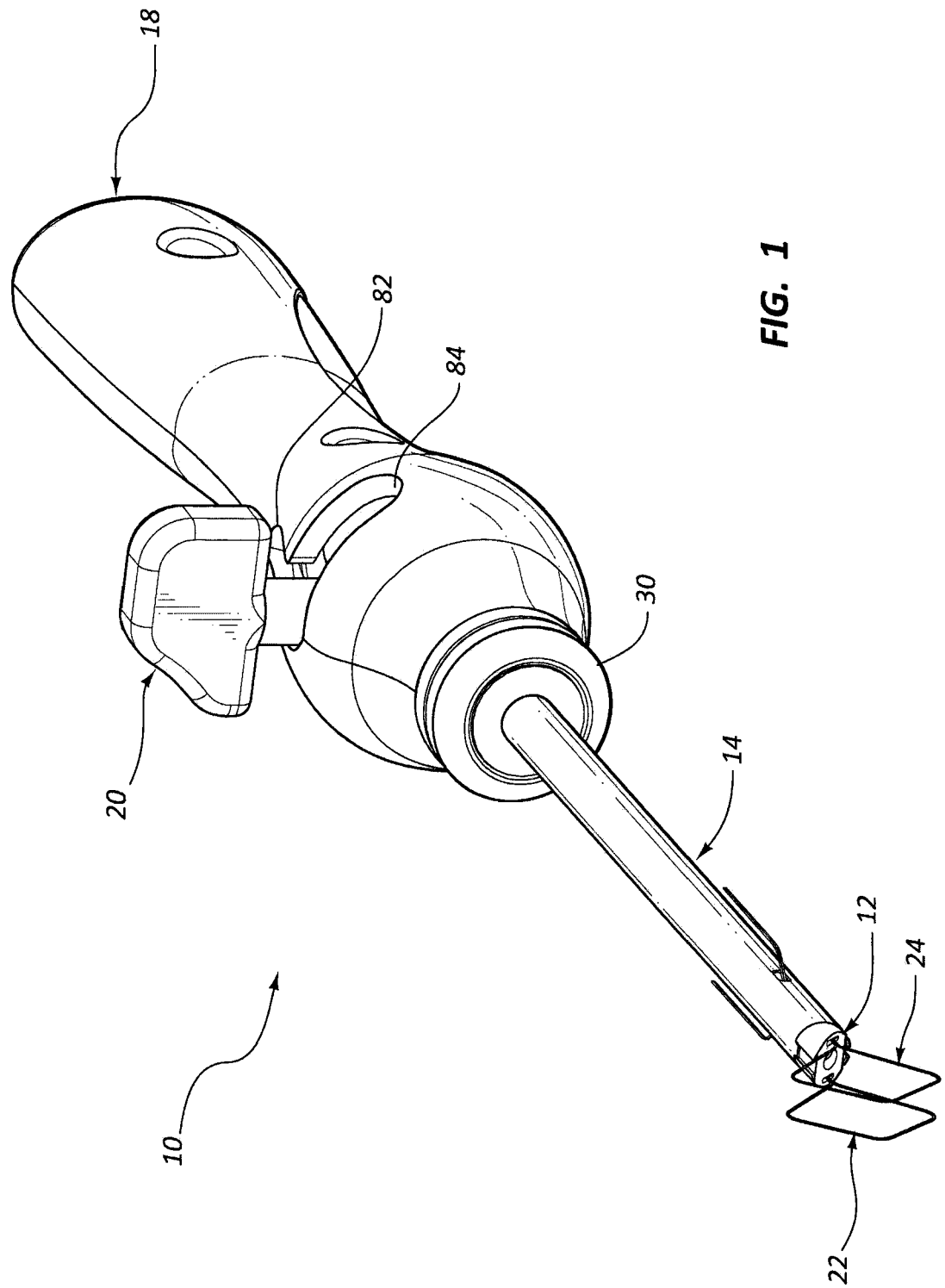
FIG. 1 is a perspective view of an example suture locking device in accordance with the present disclosure.

The suture locking devices of the present disclosure may be particularly useful for closing a tissue puncture that is positioned percutaneously below an outer tissue surface. In one application, the tissue puncture is a vessel puncture positioned with a tissue layer spaced from an outer tissue surface. The vessel puncture is accessible percutaneously through a tissue tract. The tissue puncture is closed using a knot that is tied in the suture and then advanced down the tissue tract to the tissue puncture. The tissue puncture is often hidden from view by the operator, making it difficult to confirm whether the knot is properly positioned and the tissue puncture sealed closed.

The present disclosure is directed to a device that locks at least one suture in place across a wound (e.g., to cinch closed a puncture in a vessel). The device may be constructed to help close a tissue puncture that is hidden within a tissue tract and accessible percutaneously. In one embodiment, the device is adapted to lock a pair of sutures across an opening in a wall of a vessel. The present disclosure contemplates that a medical procedure will be performed through a sheath inserted through the opening in the vessel wall to access the inside of the vessel. The device is used after the medical procedure has been completed and the sheath removed. A closure device may be used to place the suture extending through the vessel wall adjacent to the vessel opening. The device of the present disclosure may be used to advance a locking device along the suture to the vessel opening. The locking device cinches the suture to close the vessel opening and then hold the suture in tension to maintain closure of the vessel opening.

In one example, the locking device includes a two-part construction. The suture is captured between the two parts of the locking device. When the locking device is in an unlocked state, the suture is able to freely move through the locking device. When the locking device is moved into a locked position, the suture is locked in place relative to the locking device (e.g., immovable at least longitudinally).

The device may include a suture cutting feature that cuts the suture after locking the suture and/or locking device in place. The device may include a single actuator that in a first actuated position locks the two-part locking device together to lock the suture in place, and in a second actuated position cuts the suture. Locking the locking device may include actuation of the actuator along a length of the device (e.g., rotation or pivoting about a lateral axis of the device), and cutting the suture may include actuation of the actuator laterally (e.g., rotation or pivoting about a longitudinal axis of the device).

Referring now to FIGS. 1-9B, an example suture locking device 10 is shown and described. The suture locking device 10 includes a locking assembly or locking device 12, a carrier member 14, a cutting device 16, a handle 18, an actuator assembly 20, and first and second snares 22, 24. The suture locking device 10 may also include a disconnect member 26 and a biasing member 28 positioned internally, and a collar 30 interposed between the carrier member 14 and handle 18. The suture locking device 10 may also include a spacer rod 34 positioned between the carrier member 14 and the disconnect member 26.

Referring now to FIGS. 7-9B, the locking assembly 12 includes first and second locking members 40, 42. The first locking member 40 includes a distal surface 44, at least one suture aperture 46, an outer locking surface 48, and a guidewire opening 49. The second locking member 42 includes an inner locking surface 50 and an opening 52 providing access to the inner locking surface 50.

The distal surface 44 is typically arranged at an angle $\alpha_1$ relative to a longitudinal axis X of the first locking member 40. The angle $\alpha_1$ is typically in the range of about 30° to about 60°, and more preferably about 45°. The angle $\alpha_1$ is typically substantially equal to the angle at which the suture locking device 10 is advanced percutaneously through a layer of tissue to a vessel puncture. The distal surface 44 is usually configured and arranged to be parallel with an outer surface of a vessel adjacent to the vessel puncture when the suture locking device 10 is inserted at angle $\alpha_1$.

The suture apertures 46 are sized to receive at least one suture or length of suture. A suture advanced through suture aperture 46 may then be positioned along the outer locking surface 48. When the first and second locking members 40, 42 are arranged adjacent to each other as shown in FIGS. 8A-9B, a suture path 32 is defined between the outer locking surface 48 and inner locking surface 50. The suture path 32 tracks the position of the first and second snares 22, 24 shown in FIG. 6B. The suture may be captured or locked in place relative to locking assembly 12 when the first and second locking members 40, 42 are connected or locked together as shown in FIGS. 8B and 9B.

The outer and inner locking surfaces 48, 50 may have a shape and size that are, for example, substantially mirror images of each other. Typically, the outer and inner locking surfaces 48, 50 include a texture, recess, groove or other feature that defines a tortuous path for the suture and increases friction. FIGS. 7-9B illustrate a plurality of steps 51 along the outer and inner locking surfaces 48, 50. The steps 51 define a tortuous suture pathway through at least a portion of the locking assembly 12. As clearly shown in at least FIGS. 8A-9B, the steps 51 have different maximum width dimensions depending on their longitudinal positions on the outer and inner locking surfaces 48, 50. The steps 51 may increase a surface area in contact with the suture that provides increased resistance to movement of the suture relative to the locking assembly 12 when the first and second locking members 40, 42 are connected together.

The guidewire opening 49 is sized to receive a guidewire that has been prepositioned extending through the puncture in the vessel. The locking assembly 12 may move over the guidewire to a position adjacent to the vessel puncture.

The first and second locking members 40, 42 may comprise a polymer material such as, for example, propylene or other material that enhances an inference fit connection between the first and second locking members 40, 42. The first and second locking members 40, 42 may be connected together by axially moving a distal portion of the first locking member 40 through the opening 52 of the second locking member 42 until the outer and inner locking surfaces 48, 50 connect together. In some arrangements, the first locking member 40 is maintained in a fixed position relative to the carrier member 14, and the second locking member 42 is advanced distally to connect together the first and second locking members 40, 42. In other arrangements, the second locking member 42 is maintained in a fixed position and the first locking member 40 is moved proximally to provide a connection there between. Other types of connection configurations may be possible that include, for example, relative rotation or pivoting between the first and second locking members 40, 42 with or without additional relative axial movement between the first and second locking members 40, 42. Alternatively, fasteners or other attachment devices may be used to connect together the first and second locking members 40, 42.

At least one of the first and second locking members 40, 42 may include features that promote connection of the locking assembly 12 to remaining portions of the suture locking device 10 (e.g., the carrier member 14 or disconnect member 26). In one example, the second locking member 42 includes a connection protrusion 54 that assists in connecting the locking assembly 12 to the suture locking device 10. The locking assembly 12 may be disconnected from the suture locking device 10 by rotating another feature of the suture locking device 10 such as, for example, the cutting device 16, disconnect member 26, or carrier member 14.

Figure 2:
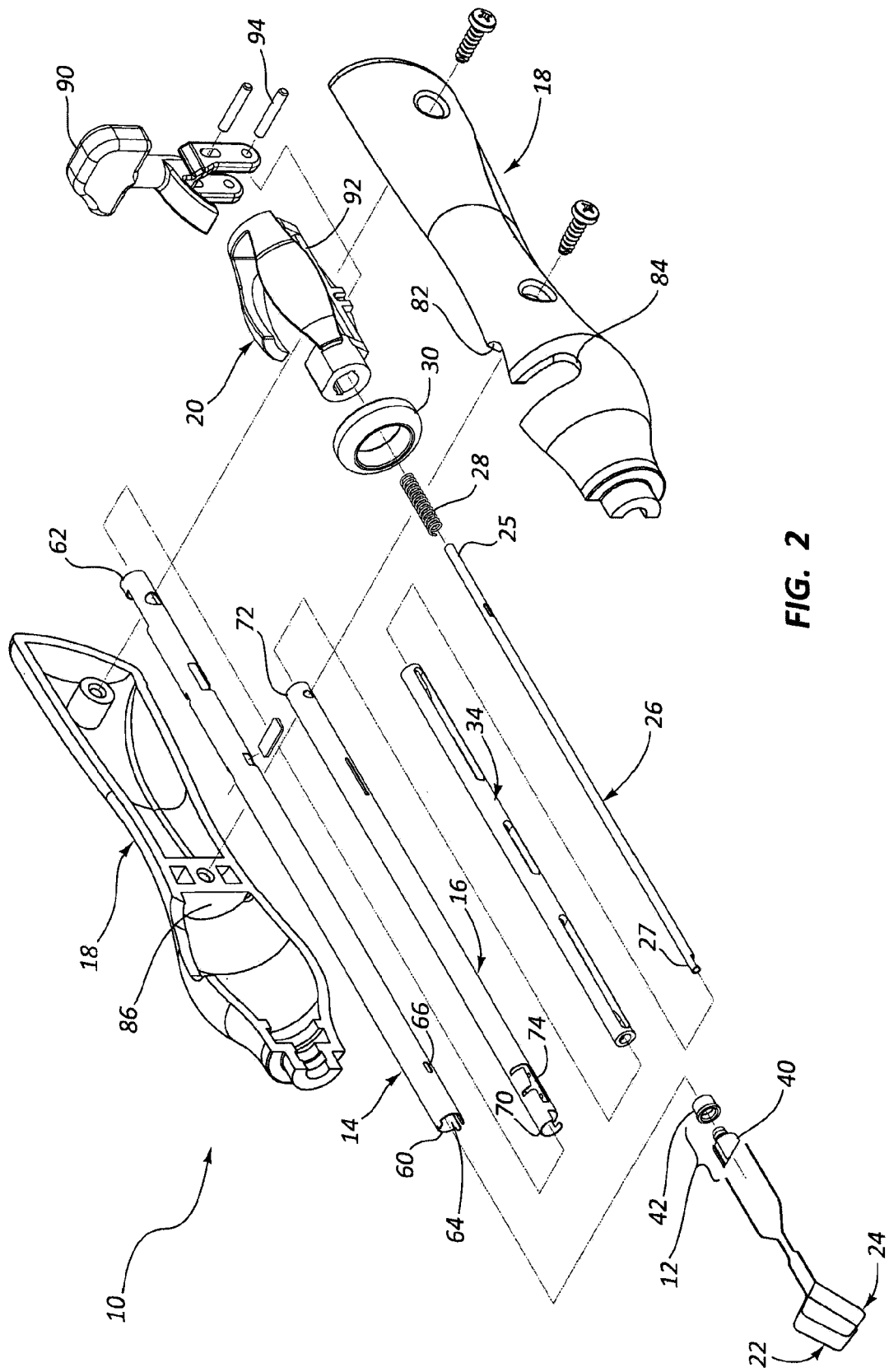
FIG. 2 is an exploded perspective view of the suture locking device of FIG. 1.
Figure 7:
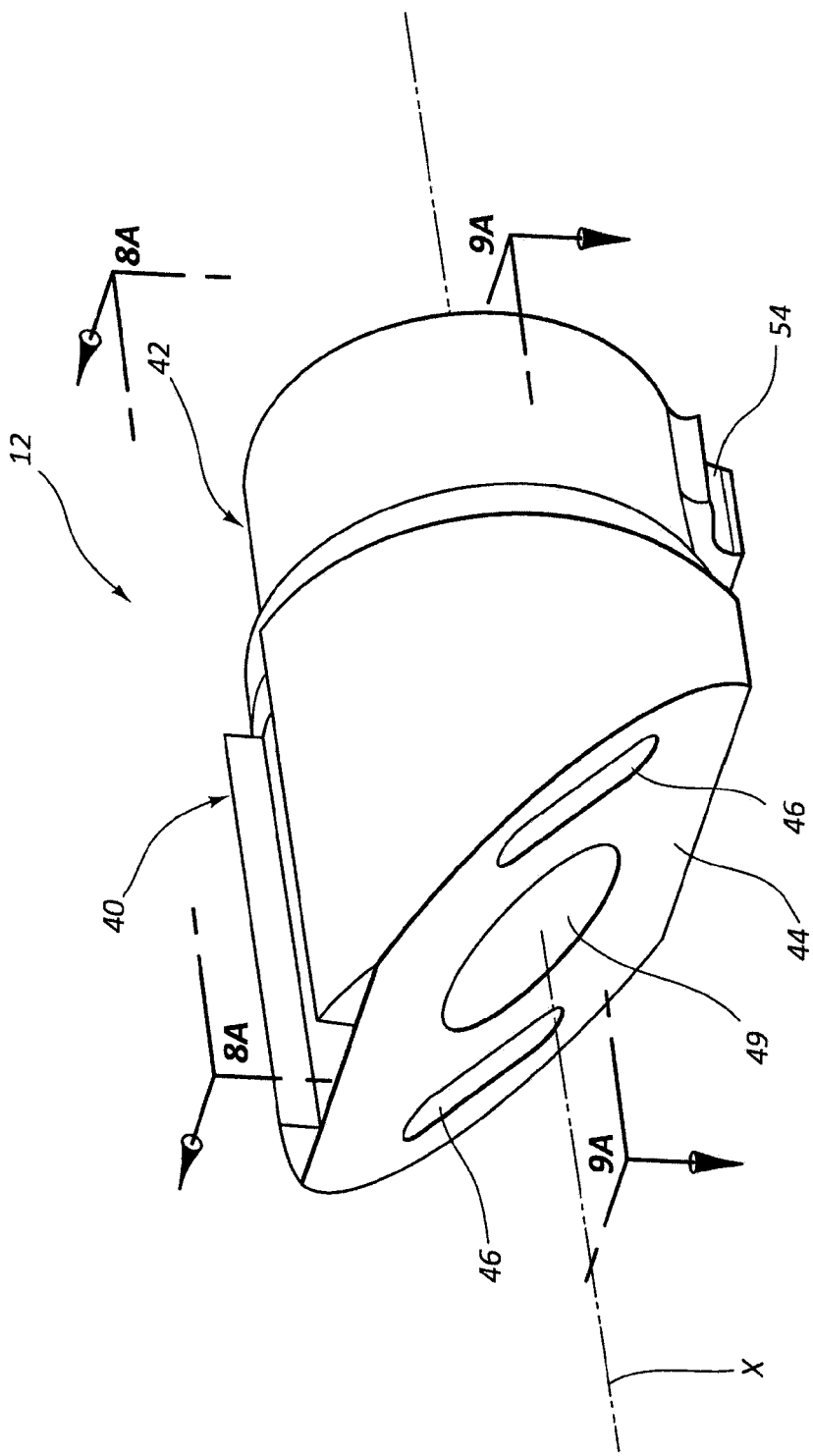
FIG. 7 is a perspective view of a locking assembly of the suture locking device of FIG. 1.

The carrier member 14 may include distal and proximal ends 60, 62, a distal opening 64, and at least one suture outlet opening 66 (see FIG. 2). The locking assembly 12 may be at least partially inserted within the distal opening 64 at the distal end 60. The proximal end 62 may extend into the handle 18 to provide a connection between the carrier member 14 and handle 18.

The suture outlet opening 66 may be positioned along the sidewall of the carrier member 14 at a location spaced proximal of the distal end 60. A suture outlet opening 66 may define a termination point for a suture path that extends from the suture aperture 46 at the first locking member 40, through a space defined between the outer and inner locking surfaces 48, 50, through an interior of the carrier member 14, and out of the suture outlet opening 66. The suture outlet opening 66 may define a fixed surface through which the sutures pass and against which the cutting device 16 operates (e.g., shears) to cut the sutures internal the carrier member 14.

The cutting device 16 may include distal and proximal end 70, 72 and a cutting surface 74. The cutting surface 74, when rotated adjacent to the suture outlet opening 66, cuts a suture captured there between. The cutting surface 74 may be positioned at the distal end 70. A proximal end 72 may extend into the handle 18 and be operable by actuation of the actuator assembly 20 between various actuated positions. In some arrangements, the actuator assembly 20 may also advance or retract the cutting device 16 axially relative to the carrier member 14.

The handle 18 includes an actuator slot 80 having a first portion 82 that permits axial movement (e.g., pivot about a lateral axis or translational movement axially) of the actuator assembly 20, and a second portion 84 that permits lateral movement (e.g., rotation in a lateral direction) of the actuator assembly 20 relative to the handle 18. The handle 18 further includes an internally positioned support surface 86. The support surface 86 may support (e.g., act as a position stop) the carrier member 14 and other features such as, for example, the actuator assembly 20 within the handle 18.

The handle 18 may be designed to promote handling by an operator with a single hand. The actuator assembly 20 may be positioned for operation by a thumb or combination of thumb and finger of an operator while the handle 18 is positioned in the operator's hand.

The actuator assembly 20 may include a lever 90, a base 92, and at least one pivot axle or pivot point 94. The entire actuator assembly 20 may be movable rotationally within the handle 18. Typically, the lever 90 is pivotally mounted at the pivot axle 94 to the base 92. The lever 90 is rotatable or pivotable between rearward (see FIG. 10B) and forward (see FIG. 12B) positions within the first portion 82 of the actuator slot 80. When in the forward position shown in FIG. 12B, the entire actuator assembly 20 may be rotated relative to the handle 18 about a longitudinal axis with the lever 90 traveling through the second portion 84 of the actuator slot 80.

Operating the actuator assembly 20 in the axial direction (e.g., pivoting forward within the first portion 82 of the actuator slot 80) moves the first and second locking members 40, 42 into connection with each other to lock the suture relative to the locking assembly 12. Rotation of the actuator assembly 20 about a longitudinal axis of the suture locking device 10 (e.g., rotating the lever 90 within the second portion 84 of the actuator slot 80) provides cutting of the suture with the cutting device 16. Rotation of the actuator assembly 20 about the longitudinal axis may also disconnect the locking assembly 12 from the suture locking device 10. Detaching the locking assembly 12 and cutting the suture with the cutting device 16 may occur concurrently so that once moved into the rotated position shown in FIG. 13B the suture locking device 10 may be removed to leave behind the locking assembly 12 locked with the suture.

The rotational release arrangement for disconnecting the locking assembly 12 from the suture locking device 10 may be constructed as a quarter turn (i.e., 90°) release mechanism. In other examples, the actuator assembly 20 may rotate relative to the handle 18 through a rotation angle in the range of about 30° to about 360°, and more preferably about 30° and about 90°.

Many alternative constructions are possible for the actuator assembly 20. For example, the actuator assembly 20 may include separate levers for the locking and cutting functions of the suture locking device. In some arrangements, a separate lever may be used to disconnect the locking assembly from the remaining portions of the suture locking device (e.g., see suture locking device 110 in FIG. 15).

The disconnect member 26 may be constructed as an elongate rod or tube positioned internal the cutting device 16 and carrier member 14. The biasing member 28 may act upon a proximal end 27 of the disconnect member 26 to force a distal end 25 of the disconnect member 26 into contact with the locking assembly 12. This distally applied force tends to promote separation of the locking assembly 12 from the rest of the suture locking device 10 upon cutting of the suture with the cutting device 16 and disconnecting the locking assembly 12 mechanically from the suture locking device 10. In other arrangements, a biasing force may be applied to other features such as, for example, the cutting device 16 to promote separation between the locking assembly 12 and the suture locking device 10.

The first and second snares 22, 24 may be mounted to the suture locking device 10 initially to assist in threading the sutures through the suture pathway of the suture locking device 10 and into a position where the operator may grasp the sutures so that the suture locking device 10 may be advanced along the sutures to the vessel puncture. The first and second snares 22, 24 each include a loop 21 at a distal end thereof, and a proximal end 23 positioned for grasping by the operator. The first and second snares 22, 24 extend through the suture apertures 46 of the first locking member 40, along a pathway defined between the outer and inner locking surfaces 48, 50 of the first and second locking members 40, 42, through the carrier member 14, and out through the suture outlet opening 66.

In operation, a pair of sutures are captured within each of the first and second snares 22, 24. The sutures are threaded into the suture locking device 10 by pulling the proximal end 23 of each of the first and second snares 22, 24, which pulls the loops 21 (and sutures positioned or captured within the loops 21) along the suture path through the locking assembly 12 and out through the suture outlet opening 66 so that the sutures are exposed for grasping by the operator. Other ways of threading the sutures along the suture path and out through the suture outlet opening 66 are possible. In at least some arrangements, the suture path does not terminate at the suture outlet opening 66, but rather extends along an entire length of the carrier member 14 and out at another location such as, for example, an opening in the handle 18.

Figure 10B:
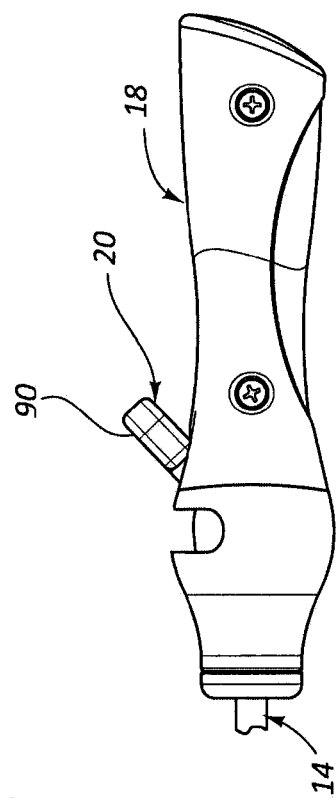
FIG. 10B is a side view of a handle the suture locking device of FIG. 10A with an actuator assembly positioned rearward.
Figure 10A:
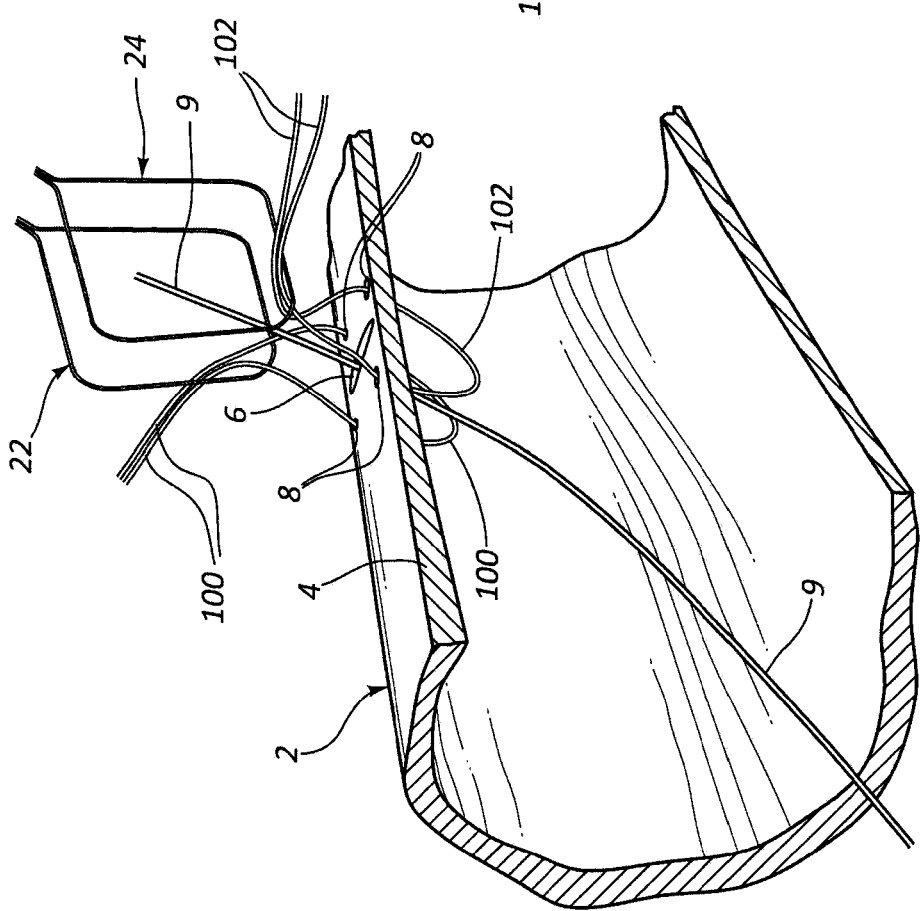
FIG. 10A is a perspective view of a vessel with a pair of sutures extending therethrough and coupled to a distal end of the suture locking device of FIG. 1.

Refer now to FIGS. 10A-14, operation of suture locking device 10 is shown and described in further detail. FIG. 10A illustrates a pair of sutures 100, 102 extending across a puncture 6 in a vessel wall 4 of a vessel 2. The sutures 100, 102 pass through a plurality of suture openings 8 that are adjacent to the puncture 6. A guidewire 9 extends through the puncture 6 and into the vessel 2. A proximal end of the guidewire 9 is advanced through the guidewire opening 49, through and the carrier member 14, and out through the handle 18 so that the suture locking device 10 may be advanced along the guidewire toward the vessel 2.

Figures 10C, 11:
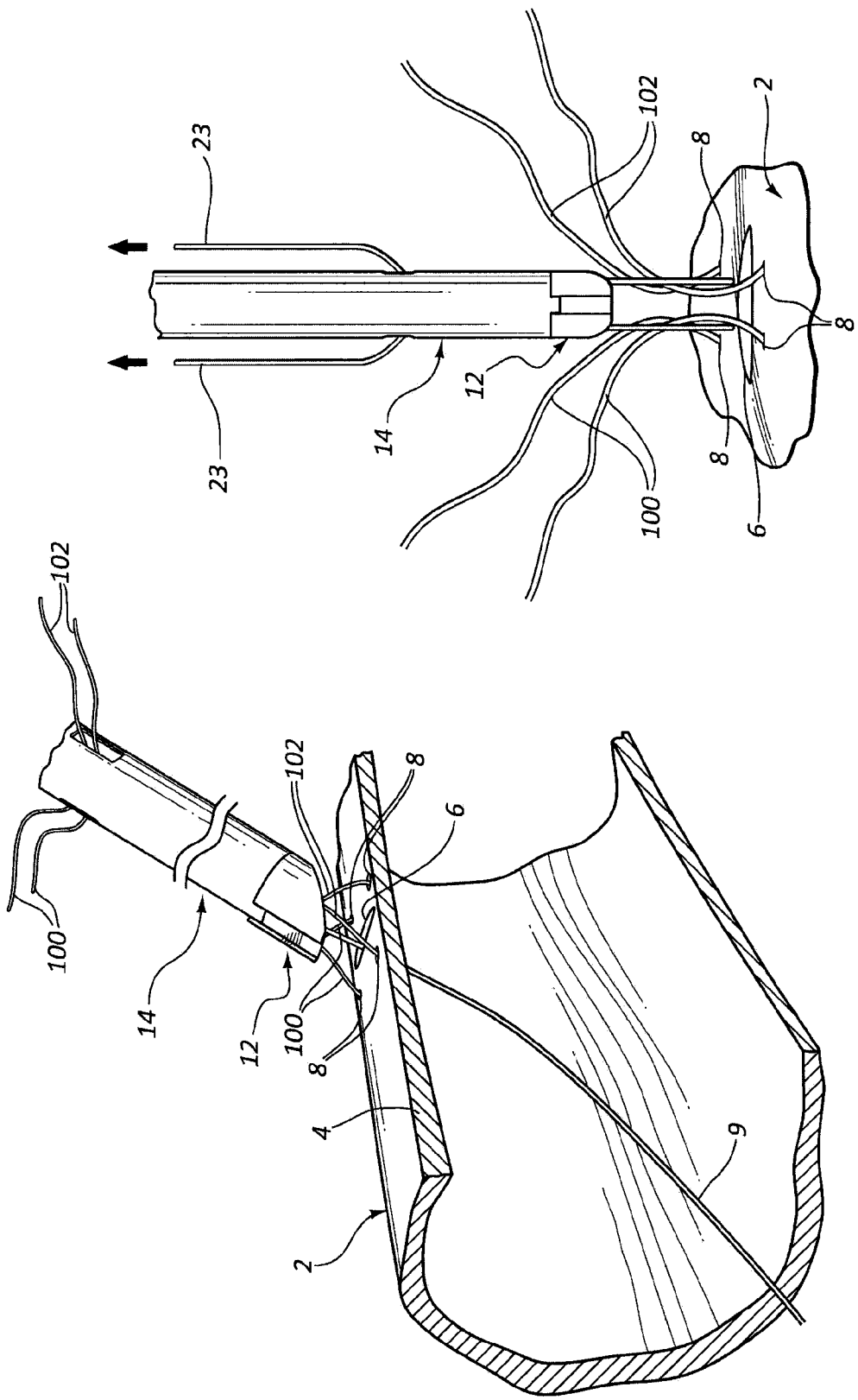
FIG. 10C is a detailed view of a distal end of the suture locking device of FIG. 10A prior to pulling the sutures into the suture locking device.
FIG. 11 illustrates the pair of sutures of FIG. 10A extending through the suture locking device.

The sutures 100, 102 are threaded through the first and second snares 22, 24, respectively, as shown in FIGS. 10A and 10C. Each of the sutures 100, 102 includes two lengths of suture, or a pair of suture lengths, that are captured in respective first and second snares 22, 24. With the sutures threaded as shown in FIGS. 10A and 10C, the first and second snares 22, 24 may be retracted proximally to pull the sutures 100, 102 through the locking assembly 12 and out through the suture outlet opening 66 of the carrier member 14 (see FIG. 11). During this threading step, the actuator assembly 20 is oriented with the lever 90 in a rearward rotated position within the first portion 82 of the actuator slot 80 as shown in FIG. 10B.

The suture locking device 10 is advanced along the guidewire 9 and sutures 100, 102 to the vessel puncture as shown in FIG. 11. In FIG. 11, the first and second locking members 40, 42 remain disconnected or in an unlocked position relative to each other to permit free passage of the sutures 100, 102 through the locking assembly 12. The operator may apply a proximally directed force to the sutures 100, 102 while advancing the suture locking device 10 distally to a position adjacent to the puncture 6. This proximally directed force applied to the sutures 100, 102 may close or at least partially close the puncture 6. Locking the sutures 100, 102 relative to the locking assembly 12 while this pressure is maintained helps keep closed the puncture 6 to help stop bleeding (i.e., hemostasis) and fluid flow through the puncture 6.

Figures 12A, 12B:
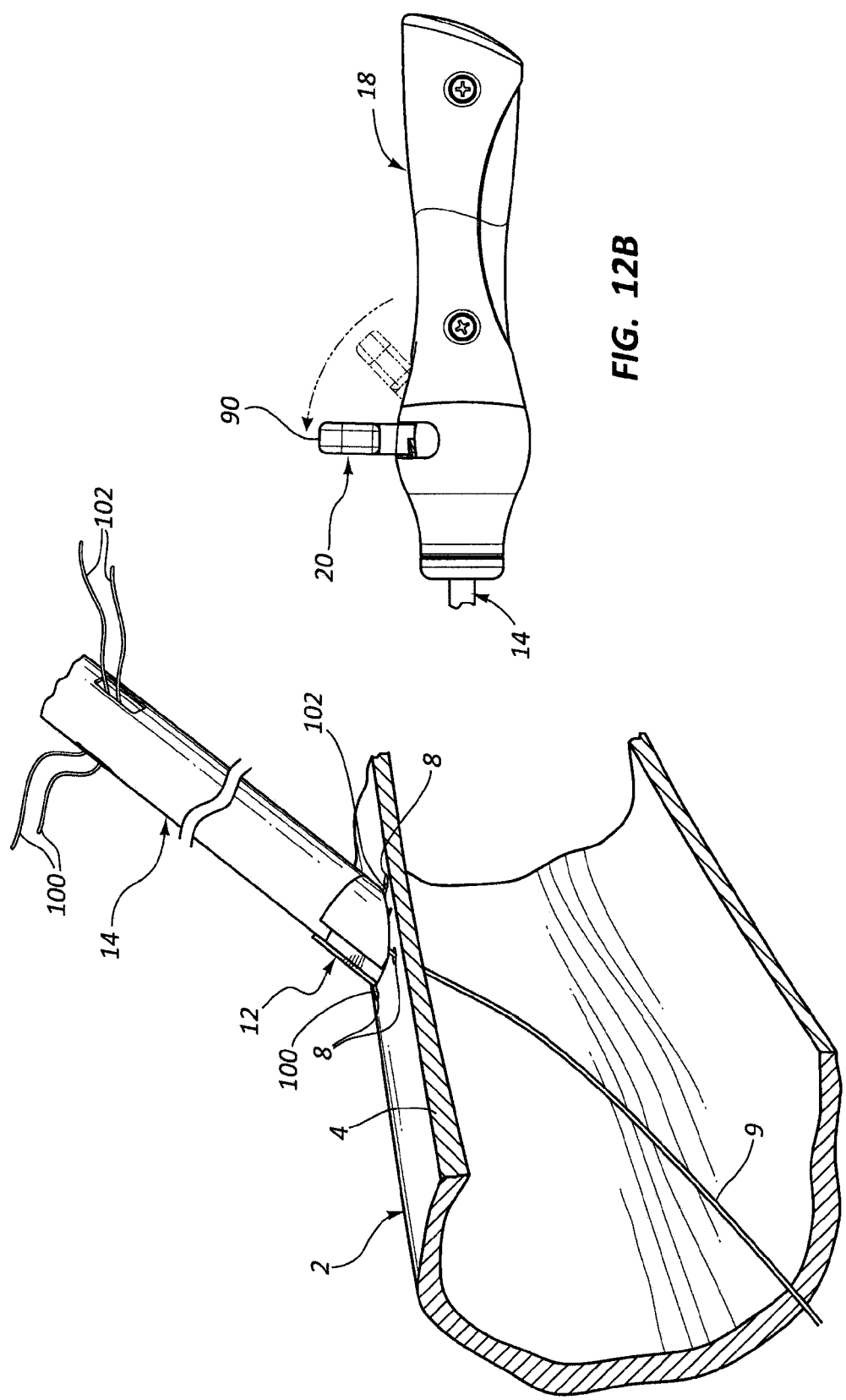
FIG. 12A illustrates the locking assembly of the suture locking device of FIG. 11 in a locked position relative to the pair of sutures.
FIG. 12B shows an actuator assembly position corresponding to the locked locking assembly shown in FIG. 12A.

Referring now to FIGS. 12A and 12B, the operator actuates the actuator assembly 20 to lock the first and second locking members 40, 42 together to lock the sutures 100, 102 relative to the locking assembly 12. FIG. 12B illustrates the lever 90 of the actuator assembly 20 moved axially forward (e.g., rotated in a forward or distal direction) to lock the second locking member 42 to the first locking member 40. The sutures 100, 102 are captured between the outer and inner locking surfaces 48, 50 to resist movement of the sutures 100, 102 relative to the locking assembly 12 (e.g., see FIG. 9B). Typically, tension in the sutures 100, 102 is maintained before, during and after locking the first and second locking members 40, 42 to maintain closure of the puncture 6.

Referring now to FIGS. 13A and 13B, the actuator assembly 20 is further operated by rotating the lever 90 about longitudinal axis X of the suture locking device 10 (i.e., in a lateral direction) to cut the sutures 100, 102 with cutting device 16. The locking assembly 12 may be disconnected from the remaining portions of the suture locking device 10 concurrently with cutting the sutures 100, 102.

Figure 14:
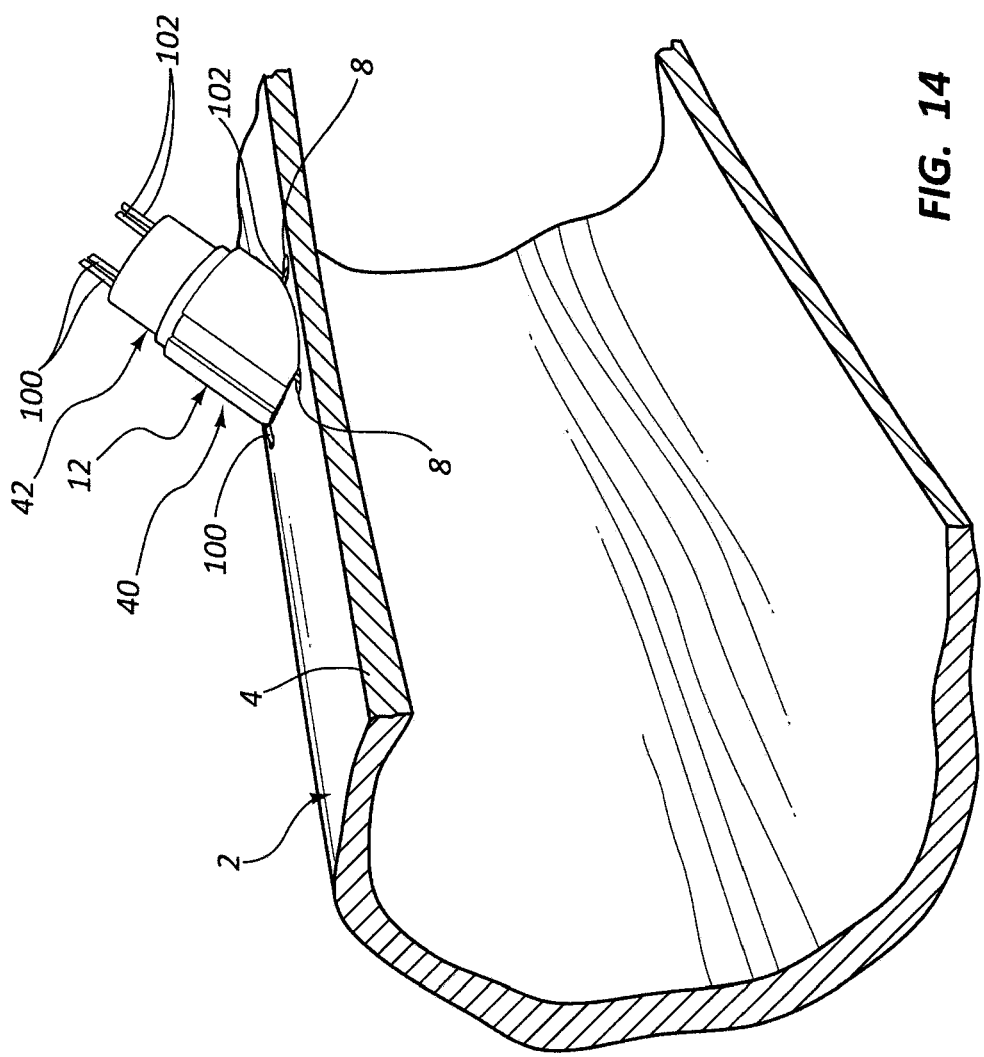
FIG. 14 illustrates the locking assembly of FIG. 13A locked on the suture and disconnected from the suture locking device.

With the sutures 100, 102 cut and the locking assembly 12 disconnected from the remaining portions of the suture locking device 10, the suture locking device 10 may be retracted along the guidewire 9 to leave behind the locking assembly 12. FIG. 14 illustrates the locking assembly 12 positioned adjacent to the vessel wall 4 with the puncture 6 cinched closed with the sutures 100, 102, and the guidewire 9 removed.

Figure 15:
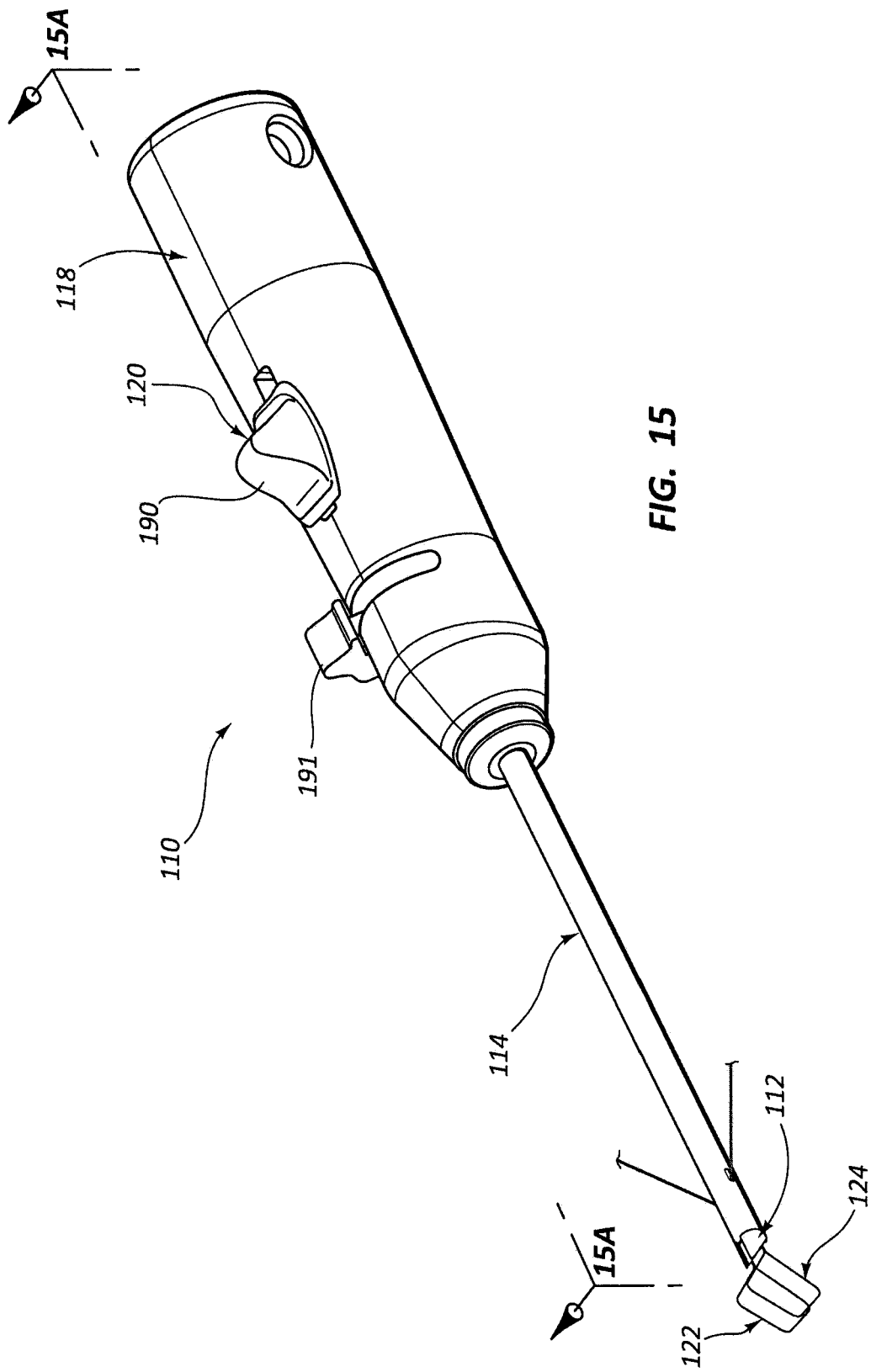
FIG. 15 is a perspective view of another example suture locking device according to the present disclosure.

Referring to FIG. 15, another example suture locking device 110 is shown having a locking assembly 112, a carrier member 114, a handle 118, and an actuator assembly 120 having first and second levers 190, 191. Each of the levers 190, 191 may perform a different function related to locking of the locking assembly 112 and cutting of at least one suture. For example, the lever 190 may move forward to lock the locking assembly 112 and fix a position of the suture relative to the locking assembly 112, and the lever 191 may be rotated about a longitudinal axis to cut the suture and/or disconnect the locking assembly 112 from the rest of the suture locking device 110.

FIGS. 16 and 17 illustrate another example cutting arrangement that includes a carrier member 214 and a cutting device 216, wherein the carrier member 214 includes a suture outlet opening 266 and cutting device 216 includes a cutting surface 274. A suture 100 passes through the suture outlet opening 266 as shown in FIG. 17. Relative rotation between the carrier member 214 and cutting device 216 captures and cuts of the suture 100.

FIGS. 18-20 illustrate another cutting arrangement that includes a carrier member 314 and a cutting device 316. The carrier member 314 includes a suture outlet opening 366. The cutting device 316 includes a cutting surface 374. The cutting surface 374 may be defined by a bent section or arm 375 that provides a constant outward directed pressure. The arm 375 may include a pre-bend radially outward. When the cutting device 316 is positioned in the carrier member 314 the arm 375 exerts a radially outward force on an internal surface of the carrier member 314 that may improve a cutting action of the cutting surface 374 relative to the suture outlet opening 366. The cutting surface 374 may be arranged at a non-parallel angle relative to a longitudinal axis of the cutting device 316 to better capture the suture between the suture outlet opening 366 and the cutting surface 374 to improve cutting of the suture.

In yet other arrangements, separate locking assemblies may be used for each of the sutures or length of suture to be locked with the suture locking device. In one example, the first locking member includes only a single suture aperture sized to receive a single length of suture or multiple lengths of suture.

In other arrangements, the actuator assembly of the suture locking device includes a plurality of biasing members or other features that provide automatic connection of features of the locking assembly, cutting of the suture, and/or disconnection of the locking assembly from the suture locking device upon release of, for example, and a trip feature of the actuator assembly.

Typically, the locking assemblies disclosed herein are configured to provide at least about 1 lb. (0.45 kg) to about 5 lbs. (2.27 kg) of pull strength on the suture to help maintain closed the vessel puncture. Preferably, the locking assemblies provide at least about 2 lbs. (0.9 kg) to about 3 lbs. (1.36 kg) of pull strength.

The pathway 32 of the suture between the first and second locking members 40, 42 typically requires at least 1 to about 3 discontinuities along the length of the suture path 32. The configuration of FIGS. 7-9B includes a plurality of discontinuities provided by the steps 51.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

What is claimed is:

1. A suture locking device, comprising:
   a carrier member;
   a locking assembly mounted at a distal end of the carrier member, the locking assembly comprising:
      a first locking member having an outer surface portion comprising a first plurality of steps, the first plurality of steps comprising a first step at a distal end of the first locking member, a second step at a proximal end of the first locking member, and a third step positioned between the first step and the second step, the first step having a first maximum width dimension, the second step having a second maximum width dimension, the third step having third maximum width dimension, wherein the first maximum width dimension is greater than the second maximum width dimension and the third maximum width dimension is less than the first maximum width dimension and greater than the second maximum width dimension;
      a second locking member having an inner surface portion comprising a second plurality of steps, the first plurality of steps of the first locking member and the second plurality of steps of the second locking member being configured to mate with each other,
      a plurality of suture apertures formed in at least one of the first and second locking members;
      a plurality of suture paths receptive of at least one suture and defined at least partially through at least one aperture in the first locking member, between the outer surface portion of the first locking member and the inner surface portion of the second locking member, and at least partially through the carrier member, each of the plurality of suture paths extending through different suture apertures; and
   an actuator assembly operable to move the first and second locking members together to lock the at least one suture relative to the locking assembly.

2. A suture locking device according to claim 1 wherein, at least one of the plurality of suture paths exit through a sidewall of the carrier member proximal of the lock assembly.

3. A suture locking device according to claim 1 further comprising a handle positioned at a proximal end of the carrier member, the actuator assembly including an actuator lever mounted to the handle.

4. A suture locking device according to claim 1 further comprising a cutting device mounted to the carrier member and operable to cut the at least one suture.

5. A suture locking device according to claim 4 wherein the cutting device is operable by the actuator assembly to cut the at least one suture within the carrier member.

6. A suture locking device according to claim 4 wherein the cutting device is operable to cut the at least one suture only after the at least one suture is locked relative to the locking assembly.

7. A suture locking device according to claim 1 further comprising at least one snare operable to pull the at least one suture into the suture locking device along at least one of the plurality of suture paths.

8. A suture locking device, comprising:
a carrier member having a longitudinal axis;
a suture locking assembly at least partially positioned in the carrier member;
a suture cutting member;
an actuator operable to lock a suture with the suture locking assembly by pivoting relative to the carrier member from a rearward position to a forward position that is longitudinally advanced relative to the rearward position along the longitudinal axis, and operable to cut the suture with the suture cutting member by laterally rotating relative to the carrier member and the longitudinal axis.

9. A suture locking device according to claim 8 wherein the suture locking assembly includes first and second locking members that define a suture path between an outer surface of the first locking member and an inner surface of the second locking member, the outer surface of the first locking member and the inner surface of the second locking member being configured to provide an interference fit connection between the first and second locking members.

10. A suture locking device according to claim 8, wherein the suture locking assembly is releasably mounted at a distal end of the carrier member.

11. A suture locking device according to claim 10 wherein the suture locking assembly is configured to be concurrently released from the carrier member when the actuator is operated to cut the suture.

* * * * *